United States Patent [19]

Tessier et al.

[11] Patent Number: 4,868,317
[45] Date of Patent: Sep. 19, 1989

[54] NOVEL DERIVATIVES

[75] Inventors: Jean Tessier, Vincennes; Jean-Pierre Demoute, Montreuil-Sous-Bois, both of France

[73] Assignee: Roussel Uclaf, Paris, France

[21] Appl. No.: 297,757

[22] Filed: Jan. 17, 1989

Related U.S. Application Data

[62] Division of Ser. No. 142,534, Jan. 7, 1988, Pat. No. 4,837,341.

[30] Foreign Application Priority Data

Jan. 9, 1987 [FR] France .................................. 87 0450
Jul. 30, 1987 [FR] France ................................ 87 10792

[51] Int. Cl.$^4$ .......................................... C07D 307/93
[52] U.S. Cl. .................................... 549/302; 549/304; 549/305
[58] Field of Search ..................... 549/302, 304, 305

[56] References Cited

U.S. PATENT DOCUMENTS 4,556,732  12/1985  Martel et al. ...................... 549/302

FOREIGN PATENT DOCUMENTS 0041283  12/1981  European Pat. Off. ............ 549/302

OTHER PUBLICATIONS

Primary Examiner—Mary C. Lee
Assistant Examiner—MarySue Howard
Attorney, Agent, or Firm—Bierman & Muserlian

[57] ABSTRACT

A compound of the formula

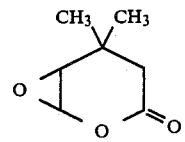

in its d, l or dl form and mixtures thereof and their preparation and their use in the synthesis of pyrethrinoids.

5 Claims, No Drawings

NOVEL DERIVATIVES

This is a division of Ser. No. 142,534 filed Jan. 7, 1988, now U.S. Pat. No. 4,837,341.

STATE OF THE ART

Related prior art is British patent application Ser. No. 2,052,479.

OBJECTS OF THE INVENTION

It is an object of the invention to provide the novel compounds of formula I and a process for their preparation.

It is a further object of the invention to use the compounds of formula I to prepare pyrethrinoid intermediates.

These and other objects and advantages of the invention will become obvious from the following detailed description.

THE INVENTION

The novel compounds of the invention are the d, l and dl forms of 5,6-epoxy-4,4-dimethyl-tetrahydro-pyr-2-one of the formula

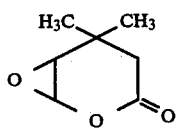

I and mixtures thereof. The d l form is preferred.

The novel process of the invention for the preparation of the compounds of formula I comprises reacting a compound of the formula

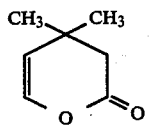

II with an epoxidizing agent to obtain a compound of formula I and optionally recovering the individual enantiomers.

Examples of suitable epoxidation agents are peracids such as peracetic acid, trifluoroperacetic acid, perphthalic acid, p-nitroperbenzoic acid, m-chloroperbenzoic acid, monopercamphoric acid and hydrogen peroxide in an alkaline solution or hexafluoroacetone hydroperoxide. Also useful are biochemical epoxidations using an isolated enzyme or a biochemical route.

In a preferred mode of the process, the epoxidation agent is a mineral or organic peracid, hydrogen peroxide along or with a mediator or with an oxidant capable of transferring an oxygen atom or an isolated biochemical agent (enzyme) or a more complex medium (microbiolgical oxidation). The most preferred epoxidation agent is m-chloroperbenzoic acid.

In a modification of the process of the invention, a compound of formula II is reacted with an epoxidation agent in the presence of a metallic catalyst and a chiral agent to obtain a non-equimolar mixture of (5R,6S) epoxy-4,4-dimethyl-tetrahydro-pyr-2-one of the formula

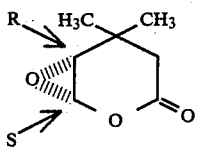

$I_A$ and its optical antipode, (5S,6R) epoxy-4,4-dimethyl-tetrahydro-pyr-2-one of the formula

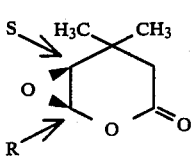

$I_B$

Because of the chiral agent, one obtains a majority of a compound of formula $I_A$ or $I_B$. The preferred metallic catalyst is hexacarbonyl molybdenum but equally useful are derivatives of titanium, vanadium, selenium or osmium. Preferred chiral agents are L(+) or D(−) dialkyl tartrates having 1 to 6 carbon atoms in each alkyl such as L(+) or D(−) diisopropyl tartrate or L(+) or (D−) diethyl tartrate.

The preferred process comprises the use of L(+) diethyl tartrate in the presence of hexacarbonyl molybdenum with tert.butyl hydroperoxide as the epoxidation agent although other epoxidation agents such as peracids or hydrogen peroxide may be used. The process permits the selective epoxidation of a non-conjugated and not α-hydroxylated double bond.

The compounds of formula I are useful as intermediates for the synthesis of compounds of the formula

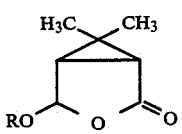

VI which are described in French Pat. No. 1,580,474 and European Pat. No. 0,023,454 and No. 0.024,241. The process for the preparation of a compound of the formula

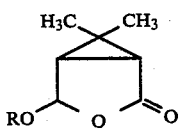

VI wherein R is selected from the group consisting of optionally unsaturated alkyl of 1 to 12 carbon atoms and optionally interrupted with a heteroatom and optionally substituted with one or more functional groups, optionally unsaturated cycloalkyl of 3 to 12 carbon atoms optionally interrupted with a heteroatom or optionally substituted with at least one functional group, aryl of up to 14 carbon atoms and aralkyl of up to 18 carbon atoms comprises reacting a compound of formula I with an alcohol of the formula

R—OH   III wherein R has the above definition to obtain a compound of the formula

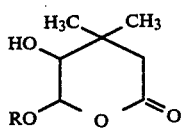

reacting the latter with a halide of the formula Z-X wherein X is a halogen and Z is $R_1$—A—, $R_1$ is selected from the group consisting of alkyl of 1 to 8 carbon atoms and optionally aryl, A is

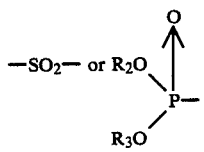

and $R_2$ and $R_3$ are individually alkyl of 1 to 8 carbon atoms to obtain a compound of the formula

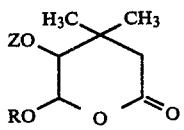

and reacting the latter with a basic agent to obtain the compound of formula VI.

When R is alkyl, it is preferably methyl, ethyl, n-propyl, isopropyl, n-butyl, tert.-butyl, n-pentyl or 1,1-dimethylallyl and when R is cycloalkyl, it is preferably cyclopropyl, cyclobutyl, cyclopentyl, cyclohexyl or menthyl. The functional group for the alkyl substituent may be halogen, —OH, —SH, —OR', —SR', —NO$_2$,

—CN, —PO$_4$H$_2$, —COAlk$_1$, —SO$_2$Alk$_2$, or —SO$_3$Alk$_3$, R' is alkyl of 1 to 8 carbon atoms, R" and R''' are individually hydrogen or alkyl of 1 to 8 carbon atoms and Alk$_1$, Alk$_2$ and Alk$_3$ are alkyl of 1 to 18 carbon atoms.

When R is alkyl interrupted by a heteroatom, it is preferably

—CH$_2$OCH$_3$, —CH$_2$—CH$_2$—O—CH$_3$,

—CH$_2$CH$_2$—OCH$_2$CH$_3$—, —CH$_2$—CH$_2$—NH—CH$_3$,

—CH$_2$—CH$_2$—N(CH$_3$)—CH$_3$ or —CH$_2$—CH$_2$—N(CH$_3$)—CH$_2$CH$_3$.

When R is aralkyl, it is preferably benzyl and when R is aryl, it is preferably phenyl. X is preferably chlorine or bromine.

In the definition of Z, $R_1$, $R_2$ and $R_3$, are preferably methyl, ethyl, n-propyl, isopropyl, tert.-butyl, n-butyl or phenyl optionally substituted with one or more alkyl.

The basic agent for reaction with the compound of formula V is a metal hydride, an alkali metal or alkaline earth metal alcoholate, an organometallic derivative, an alkali metal or alkaline earth metal hydroxide or carbonate or a tertiary amide. The preferred basic agents are sodium hydroxide and potassium hydroxide.

In a preferred mode of the process, the compound of the formula I is racemic, the compound of formula IV is racemic with the RO— and —OH having the trans form, the compound of formula V is racemic and the ZO— and —OR have the trans form and the compound of formula VI is racemic. R is preferably methyl, ethyl or tert.-butyl and Z is —SO$_2$CH$_3$.

The process may be used to prepare in an enantioselective fashion the lactone of (1R, cis) 3,3-dimethyl-2-(dihydroxymethyl)-cyclopropane carboxylic acid of the formula

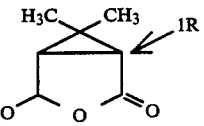 Product P which is useful for the synthesis of biologically active pyrethrinoids as described in French Pat. No. 1,580,474. Product P may be prepared by the following reaction scheme.

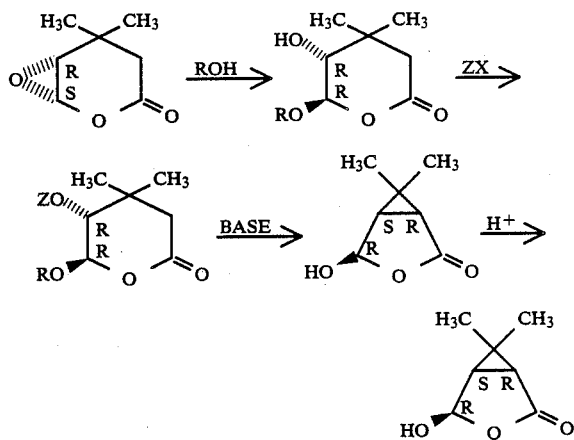

In the following examples there are described several preferred embodiments to illustrate the invention. However, it should be understood that the invention is not intended to be limited to the specific embodiments.

EXAMPLE I

Racemic 5,6-epoxy-4,4-dimethyl-tetrahydro-pyr-2-one

A solution of 43.15 g of m-chloroperbenzoic acid in 25.2 g of 4,4-dimethyl-3,4-dihydro-2-pyrone at 0° C. was stirred for 3 hours while allowing the temperature to rise to room temperature and was then vacuum filtered. The product was empasted with methylene chloride and the filtrate was washed with an aqueous sodium thiosulfate, then with water. The organic phase was dried and evaporated to dryness under reduced pressure to obtain 28.5 g of raw product which was chromatographed over silica gel and eluted with an hexane-isopropyl ether to obtain 23.08 g of racemic 5,6-epoxy-4,4-dimethyl-tetrahydro-pyr-2-one melting towards 22° C.

NMR Spectrum (CDCl$_3$)

Peaks at 1.13–1.26 ppm (hydrogens of geminal methyls); at 2.03 to 2.75 ppm (3-hydrogen), at 5.22–5.27 ppm (6-hydrogen); at 2.98 to 3.05 ppm (5-hydrogen).

EXAMPLE 2

(5R,6S)-epoxy-4,4-dimethyl-tetrahydro-pyr-2-one (I$_A$) and (5S,6R)-epoxy-4,4-dimethyl-tetrahydro-pyr-2-one (I$_B$)

25 ml of 2.9M of tert.butyl hydroperoxide in toluene were added at 0° C. to a solution of 2.52 g of 4.4-dimethyl-3,4-dihydro-2-pyrone, 25 ml of toluene preserved by siliporite, 4.12 g of L(+) diethyl tartrate and 110 mg of molybdenum hexacarbonyl and after the mixture returned to room temperature, it was stirred for 20 hours. The mixture was poured into a solution of 10 g of tartaric acid, 25 g of ferric sulfate and 100 ml of water and the mixture was rinsed with toluene and was stirred for one hour at 15° to 20° C. The decanted aqueous phase was extracted with toluene and the organic phase was washed with water, dried and evaporated to dryness to obtain an oil. The oil was chromatographed over silica and eluted with a 1-1 hexane-isopropyl ether mixture to obtain a product with an RF=0.15, The solvent was evaporated to obtain 436 mg of a product which was chromatographed again and eluted with an 85-15 hexane-ethyl acetate mixture to obtain a product with an Rf=0.2. Evaporation of the solvent under reduced pressure yielded 232 mg of product melting at 22° C. and having a specific rotation of $[\alpha]^{20} = -33° \pm 2°$ (c=0.6% in toluene). The ratio of products I$_A$ to product I$_B$ is 3:2.

EXAMPLE 3

Using the procedure of Example 2, D(−) diethyl tartrate was reacted to obtain a mixture of the same product in a ratio of product I$_A$ to product I$_B$ of 2:3.

EXAMPLE 4

Using the procedure of Example 2. L(+) tartrate of diethyl was replaced by L(+) tartrate of diisopropyl to obtain a result similar to Example 2.

In Examples 2, 3, and 4, the pure enantiomer was evaluated using NMR spectrum in the presence of 20% of tris [3-(trifluoromethylhydroxymethylene) (+) camphorate] Europium III EU (tfc)$_3$.

| | Frequencies in CDCl$_3$ in ppm | |
|---|---|---|
| 5R 6S Isomer | | 5S 6R Isomer |
| protons of methyls | 1.28 and 1.38 | 1.28 and 1.42 |
| protons in 3 | 2.54 (d) | and 2.92 (d) |
| protons in 5 | 3.38 | 3.42 |
| protons in 6 | 5.71 | 5.59 (d) |

EXAMPLE 5 dl 6-methoxy-5-hydroxy-4,4-dimethyl-tetrahydro-pyr-2-one

A drop of p-toluene sulfonic acid was added at −15° C. to a solution of 1.42 g of 5.6-epoxy-4,4-dimethyl-tetrahydro-pyr-2-one melting at ≈22° C., 14 ml of methylene chloride and 320 mg of methanol and the mixture was stirred for 3½ hours at −10° C. 0.4 ml of methanol were added and the mixture was stirred at −10° C. for 16 hours. 40.4 ml of methanol and a little p-toluene sulfonic acid were added and the mixture was stirred for 48 hours while letting the temperature rise to room temperature. The mixture was decanted and the liquid phase was washed with aqueous saturated sodium bicarbonate solution, then with water, was dried and evaporated to dryness under reduced pressure. The 1.45 g of residue was chromatographed over silica and was eluted with a 1-1 mixture of hexane-ethyl acetate to obtain 1.42 g of dl 6-methoxy-5-hydroxy-4,4-dimethyl-tetrahydro-pyr-2-one melting at 72° C. and having a Rf=0.20.

NMR Spectrum

Peak at 3.6 ppm (hydrogens of —OCH$_3$).

NMR Spectrum in (CDCl$_3$)

Peaks at 1.06–1.1 ppm (hydrogens of geminal methyls); at 2.2–2.4 and 2.5–2.77 ppm (3-hydrogens); at 4.95–5.06 ppm (6-hydrogens); at 3.4–3.5 ppm (5-hydrogens).

EXAMPLE 6

6,6-dimethyl-4-isopropoxy-3-oxa-bicyclo[3,1,0]hexan-2-one

STEP A: dl 6-isopropoxy-5-hydroxy-4,4-dimethyl-tetrahydro-pyr-2-one

A mixture of 7 g of 5,6-epoxy-4,4-dimethyl-tetrahydro-pyr-2-one, 35 ml of isopropanol and 350 mg of p-toluene sulfonic acid was stirred at room temperature for 23 hours and was diluted with water. The mixture was extracted with methylene chloride and the combined extracts were washed with aqueous saturated sodium bicarbonate solution, was dried and evaporated to dryness under reduced pressure. The 9.18 g of residue was chromatographed over silica and was eluted with a 1-1 mixture of hexane-ethyl acetate to obtain 2.597 g of dl 6-isopropoxy-5-hydroxy-4,4-dimethyl-tetrahydro-pyr-2-one melting at 50° C.

NMR Spectrum in CDCl$_3$

Peaks at 1.06 to 1.31 ppm (hydrogens of geminal methyls); at 2.38–2.41 ppm (3-hydrogen); at 3.4–3.5 ppm (5-hydrogen); at 5.1–5.2 ppm (6-hydrogen).

STEP B: 6-isopropoxy-5-methylsulfonyloxy-4,4-dimethyl-tetrahydro-pyr-2-one

A mixture of 1.556 g of the product of Step A, 7.5 ml of pyridine and 1 ml of methane sulfonyl chloride was stirred for 3 hours and was then diluted with N hydrochloric acid. The mixture was extracted with methylene chloride and the organic phase was washed with water, dried and evaporated to dryness under reduced pressure to obtain 2.096 g of 6-isopropoxy-5-methylsulfonyloxy-4,4-dimethyl-tetrahydro-pyr-2-one melting at 75° C.

NMR Spectrum in CDCl$_3$

Peaks at 1.06 to 1.31 ppm (hydrogens of geminal methyls); at 2.38–2.41 ppm (3-hydrogen); at 3.4–3.5 ppm (5-hydrogen); at 5.1–5.2 ppm (6-hydrogen); at 1.23 and 1.27 ppm (hydrogens of methyls of isopropoxy); at 4.14 ppm (hydrogen of

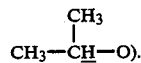

STEP C: Racemic 6,6-dimethyl-4-isopropoxy-3-oxa-bicyclo[3,1,0]hexan-2-one

A mixture of 1.94 g of the product of Step B, 10 volumes of methylene chloride containing 2.5% by weight of triethylbutylammonium chloride and 5 volumes of 50% sodium hydroxide solution was stirred while following the reaction evolution in CCM. At the end of the reaction the mixture was diluted with aqueous sodium chloride solution and was extracted with methylene chloride. The organic phase was washed with aqueous sodium chloride solution, dried and evaporated to dryness under reduced pressure. The residue was chromatographed over silica and was eluted with a 1-1 mixture of hexane-ethyl acetate to obtain 908 mg of racemic 6,6-dimethyl-4-isopropoxy-3-oxa-bicyclo[3,1,0-]hexane-2-one melting toward 50° C.

NMR Spectrum CDCl3

Peaks at 1.17–1.2 ppm (hydrogens of geminal methyls); at 2.02 ppm (1- and 5-hydrogens of hexane); at 5.27 ppm (hydrogen of carbon attached to isopropoxy); 3.82 to 4.21 ppm (hydrogen of

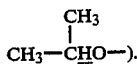

).

EXAMPLE 7

6,6-Dimethyl-4-(1,1-dimethylethoxy)-3-oxa-bicyclo[3,1,0]hexan-2-one

STEP A: 6-(1,1-dimethylethoxy)-5-hydroxy-4,4-dimethyl-tetrahydro-pyr-2-one

A mixture of 500 mg of 5,6-epoxy-4,4-dimethyl-tetrahydro-pyr-2-one, 5 ml of 1,1-dimethyl ethanol and 2.5 mg of p-toluene sulfonic acid was stirred for 41 hours at room temperature and 1 ml of pyridine was then added. The mixture was evaporated to dryness under reduced pressure to obtain 6-(1,1-dimethylethoxy)-5-hydroxy-4,4-dimethyl-tetrahydro-pyr-2-one which was used as is for the next step.

STEP B: 6(1,1-dimethylethoxy)-5-methylsulfonyloxy-4,4-dimethyl-tetrahydro-pyr-2-one A mixture of the product of Step A, 5 ml of pyridine and 1 ml of methanesulfonyl chloride was stirred for 3½ hours and was then diluted with N hydrochloric acid. The mixture was extracted with methylene chloride and the organic phase was washed with water, dried and evaporated to dryness under reduced pressure. The 677 mg of residue was chromatographed over silica and was eluted with a 7-3 mixture of hexane-ethyl acetate to obtain 410 mg of 6-(1,1-dimethylethoxy)-5-methylsulfonyloxy-4,4-dimethyl-tetrahydro-pyr-2-one melting at 64° C.

NMR Spectrum in CDCl3

Peaks at 1.06 to 1.20 ppm (hydrogens of geminal methyls); at 2.23 to 2.56 ppm (3-hydrogen); at 5.58 ppm (6-hydrogen) at 4.5 ppm (5-hydrogen); at 3.13 ppm (hydrogens of CH3O2SO—).

STEP C: 6,6-dimethyl-4-(1,1-dimethylethoxy)-3-oxa-bicyclo[3,1,0]hexan-2-one Using the procedure of Step C of Example 6, 100 mg of the product of step B were reacted to obtain 52 mg of 6,6-dimethyl-4-(1,1-dimethylethoxy)-3-oxa-bicyclo[3,1,0]hexan-2-one melting at 115° C.

NMR Spectrum in CDCl3

Peaks at 1.14 to 1.19 ppm (hydrogens of geminal methyls); at 2.23 to 2.56 ppm (1- and 3-hydrogens of cyclopropane); at 5.36 ppm (hydrogens of carbon attached to 1,1-dimethylethoxy); at 1.3 ppm (hydrogens of methyls of 1,1-dimethylethoxy).

Various modifications of the products and processes of the invention may be made without departing from the spirit or scope thereof and it should be understood that the invention is intended to be limited only as defined in the appended claims.

What we claim is:

1. A process for the preparation of a compound of the formula

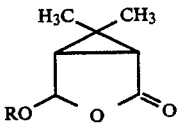

wherein R is selected from the group consisting of alkyl of 1 to 12 carbon atoms alkenyl and alkynyl of 2 to 12 carbon atoms and uninterrupted or interrupted with a heteroatom and unsubstituted or substituted with at least one functional groups, cycloalkyl of 3 to 12 carbon atoms unsubstituted or substituted with at least one functional group, aryl of up to 14 carbon atoms and hydrocarbyl aralkyl of up to 18 carbon atoms comprises reacting a compound of the formula

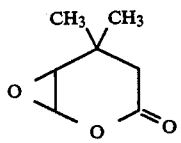

in its d, l or dl form and mixtures thereof with an alcohol of the formula

wherein R has the above definition to obtain a compound of the formula

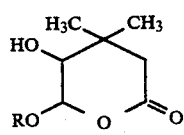

reacting the latter with a halide of the formula Z-X wherein X is a halogen and Z is R1—A—, R1 is selected from the group consisting of alkyl of 1 to 8 carbon atoms and aryl, A is

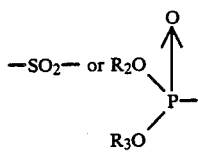

and $R_2$ and $R_3$ are individually alkyl of 1 to 8 carbon atoms to obtain a compound of the formula

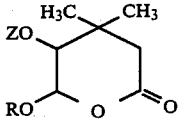

and reacting the latter with a basic agent to obtain the compound of formula VI.

2. The process of claim 1 wherein the compound of formula I is racemic, the compound of formula IV is racemic with the RO— and —OH having the trans form, the compound of formula V is racemic and the ZO— and —OR have the trans form and the compound of formula VI is racemic.

3. The process of claim 2 wherein R is methyl or ethyl or tert.butyl.

4. The process of claim 2 wherein Z is —SO$_2$CH$_3$.

5. The process of claim 3 wherein Z is —SO$_2$CH$_3$.

* * * * *